(12) United States Patent
Linares

(10) Patent No.: US 8,328,875 B2
(45) Date of Patent: Dec. 11, 2012

(54) COMBINATION MALE/FEMALE HIP JOINT AND INSTALLATION KIT

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 234 days.

(21) Appl. No.: 12/649,456

(22) Filed: Dec. 30, 2009

(65) Prior Publication Data

US 2011/0160868 A1 Jun. 30, 2011

(51) Int. Cl.
*A61F 2/32* (2006.01)
(52) U.S. Cl. .................. 623/22.15; 623/22.11
(58) Field of Classification Search .... 623/22.11–22.18; A61F 2/32
See application file for complete search history.

(56) References Cited

U.S. PATENT DOCUMENTS

| | | | |
|---|---|---|---|
| 2,667,644 A | 2/1954 | Johnson | |
| 3,973,277 A | 8/1976 | Semple et al. | |
| 4,483,023 A | 11/1984 | Hoffman, Jr. et al. | |
| 4,501,031 A | 2/1985 | McDaniel et al. | |
| 4,665,951 A | 5/1987 | Ellis et al. | |
| 4,744,793 A | 5/1988 | Parr et al. | |
| 4,778,473 A | 10/1988 | Matthews et al. | |
| 4,792,336 A | 12/1988 | Hlavacek et al. | |
| 4,828,562 A | 5/1989 | Kenna | |
| 4,851,005 A | 7/1989 | Hunt et al. | |
| 4,883,486 A | 11/1989 | Kapadia et al. | |
| 5,004,474 A | 4/1991 | Fronk et al. | |
| 5,078,745 A | 1/1992 | Rhenter et al. | |
| 5,171,325 A | 12/1992 | Aulie | |
| 5,263,984 A | 11/1993 | Li et al. | |
| 5,282,867 A | 2/1994 | Mikhail | |
| 5,376,119 A | 12/1994 | Zimmermann et al. | |
| 5,389,107 A | 2/1995 | Nassar et al. | |
| 5,417,693 A | 5/1995 | Sowden et al. | |
| 5,486,197 A | 1/1996 | Le et al. | |
| 5,554,194 A | 9/1996 | Sanders | |
| 5,571,191 A | 11/1996 | Fitz | |
| 5,575,819 A | 11/1996 | Amis et al. | |
| 5,676,702 A | 10/1997 | Ratron et al. | |
| 5,728,175 A | 3/1998 | Rincoe | |
| 5,800,566 A | 9/1998 | Gramnas et al. | |
| 5,879,404 A | 3/1999 | Bateman et al. | |

(Continued)

FOREIGN PATENT DOCUMENTS

WO 2009039164 A1 3/2009

*Primary Examiner* — Christopher D Koharski
*Assistant Examiner* — Jason-Dennis Stewart
(74) *Attorney, Agent, or Firm* — Gifford, Krass, Sprinkle, Anderson & Citkowski, P.C.

(57) ABSTRACT

A hip implant assembly including body exhibiting a substantially spherical shaped ball and an elongated stem. An annular defining rim separates the ball from the stem and abuts, in a maximum inserting condition, an exterior surface of a reconditioned femur upon inserting the stem within an interior passageway associated with the femur. A three dimensional and interior volume defining support secures around the ball in a universally articulating permitting fashion, the support being fixed to a reconditioned acetabulum socket associated with an ilium bone by interconnecting posts and anchors established between the fixed support and the reconditioned surface of the acetabulum. A corresponding installation kit assists the preparation of the femur and ilium bones defining the hip joint, as well as the installation of the implant body into the upper conditioned femur end and the outer socket support to a reconditioned acetabulum defined in the ilium bone.

14 Claims, 12 Drawing Sheets

U.S. PATENT DOCUMENTS

| | | |
|---|---|---|
| 5,921,358 A | 7/1999 | Gramnas et al. |
| 6,001,106 A | 12/1999 | Ryan et al. |
| 6,010,535 A | 1/2000 | Shah |
| 6,190,411 B1 | 2/2001 | Lo et al. |
| 6,245,109 B1 | 6/2001 | Mendes et al. |
| 6,325,804 B1 | 12/2001 | Wenstrom, Jr. et al. |
| 6,383,223 B1 | 5/2002 | Baehler et al. |
| 6,626,942 B1 | 9/2003 | Edberg et al. |
| 6,645,251 B2 | 11/2003 | Salehi et al. |
| 6,840,962 B1 | 1/2005 | Vacanti et al. |
| 6,939,379 B2 | 9/2005 | Sklar |
| 7,044,983 B1 | 5/2006 | Cheng et al. |
| 7,056,340 B2 | 6/2006 | McKernan et al. |
| 7,066,958 B2 | 6/2006 | Ferree |
| 7,087,091 B1 | 8/2006 | Chen et al. |
| 7,101,398 B2 | 9/2006 | Dooris et al. |
| 7,153,327 B1 | 12/2006 | Metzger |
| 7,175,666 B2 | 2/2007 | Yao |
| 7,329,281 B2 | 2/2008 | Hays et al. |
| 7,331,995 B2 | 2/2008 | Eisermann et al. |
| 7,708,781 B2 | 5/2010 | Scheker |
| 2001/0051831 A1 | 12/2001 | Subba Rao et al. |
| 2002/0013627 A1 | 1/2002 | Geistlich et al. |
| 2002/0143402 A1* | 10/2002 | Steinberg ............... 623/22.16 |
| 2003/0130741 A1 | 7/2003 | McMinn |
| 2004/0024460 A1 | 2/2004 | Ferree |
| 2004/0225370 A1* | 11/2004 | Cruchet et al. ............ 623/22.18 |
| 2005/0081867 A1 | 4/2005 | Murphy |
| 2005/0187620 A1 | 8/2005 | Pai et al. |
| 2005/0192674 A1 | 9/2005 | Ferree |
| 2005/0261777 A1* | 11/2005 | Jones et al. ............ 623/22.32 |
| 2006/0058886 A1 | 3/2006 | Wozencroft |
| 2006/0074423 A1 | 4/2006 | Alleyne et al. |
| 2006/0149370 A1 | 7/2006 | Schmieding et al. |
| 2007/0005137 A1 | 1/2007 | Kwak |
| 2007/0088442 A1* | 4/2007 | Cima et al. ............ 623/18.11 |
| 2008/0234830 A1* | 9/2008 | Hershberger et al. ...... 623/22.15 |
| 2009/0039164 A1 | 2/2009 | Herwig et al. |
| 2009/0088865 A1 | 4/2009 | Brehm |
| 2009/0292364 A1 | 11/2009 | Linares |

* cited by examiner

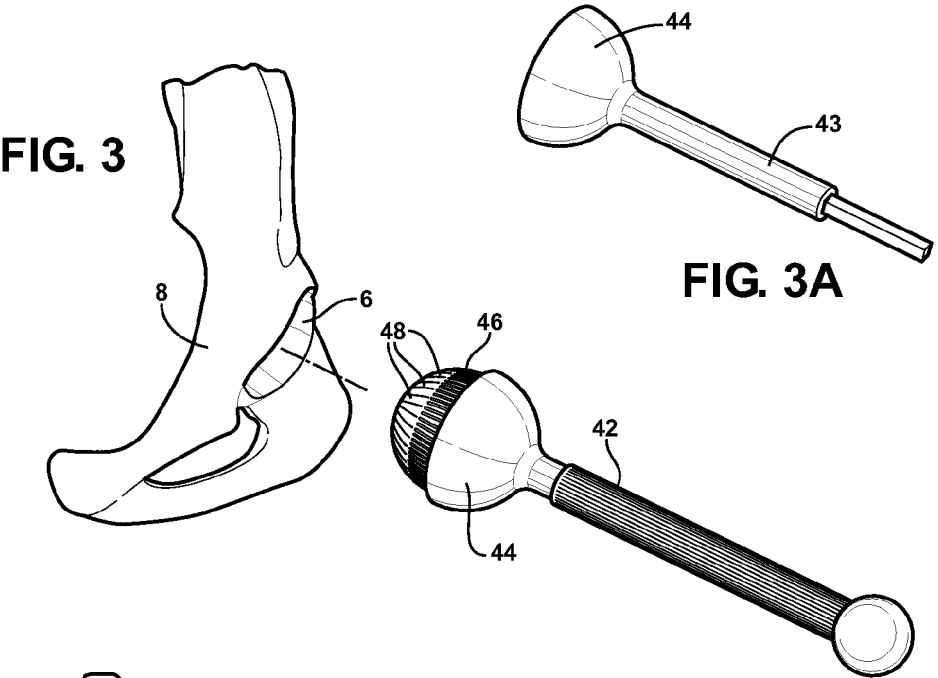
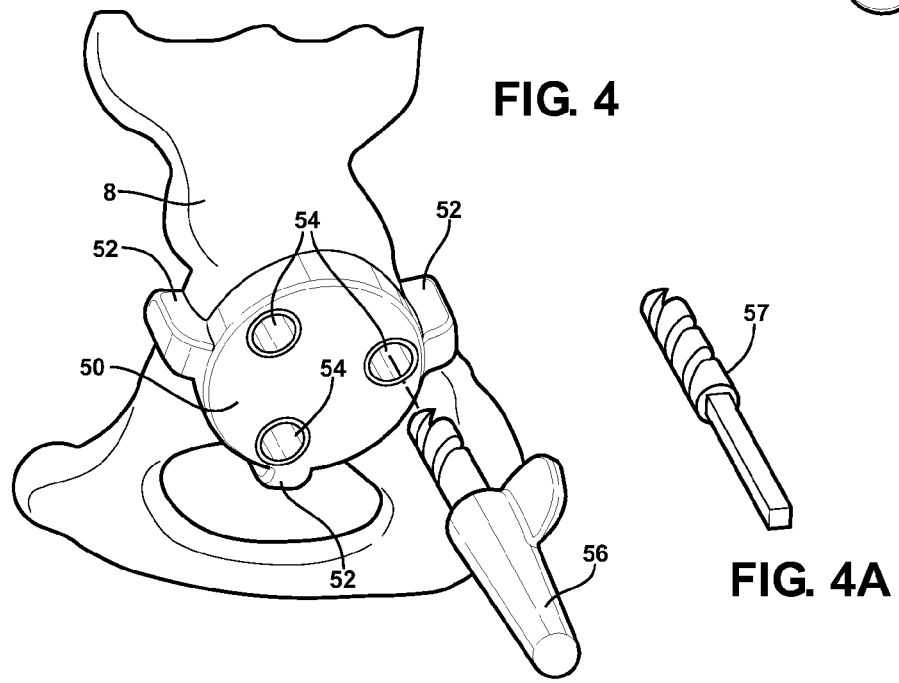

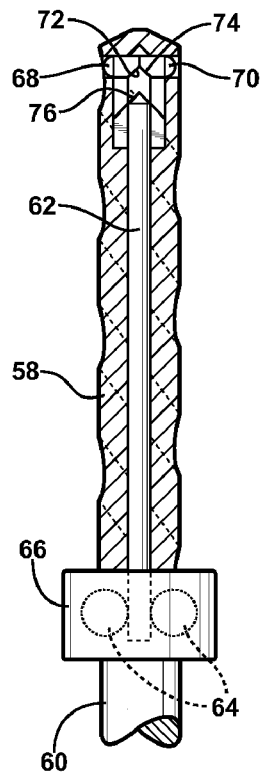
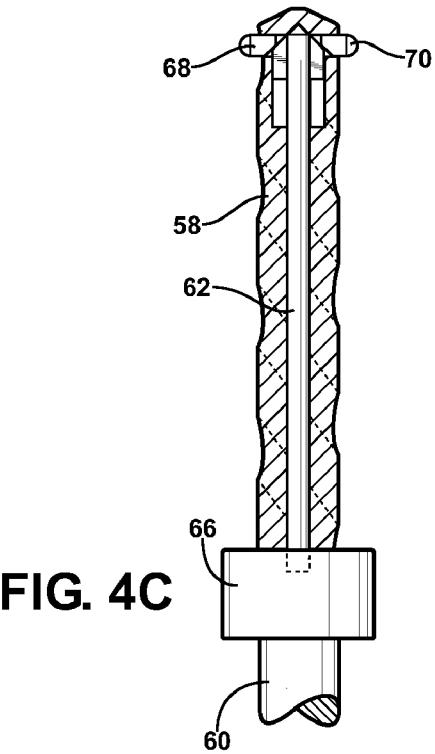
FIG. 4B  FIG. 4C
FIG. 4D  FIG. 4E  FIG. 4F
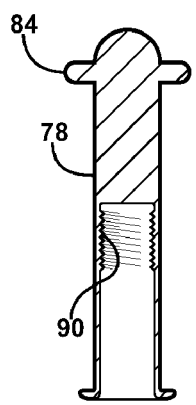
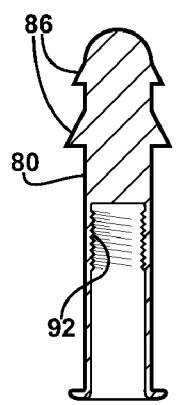
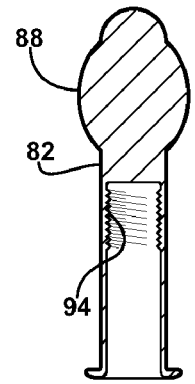

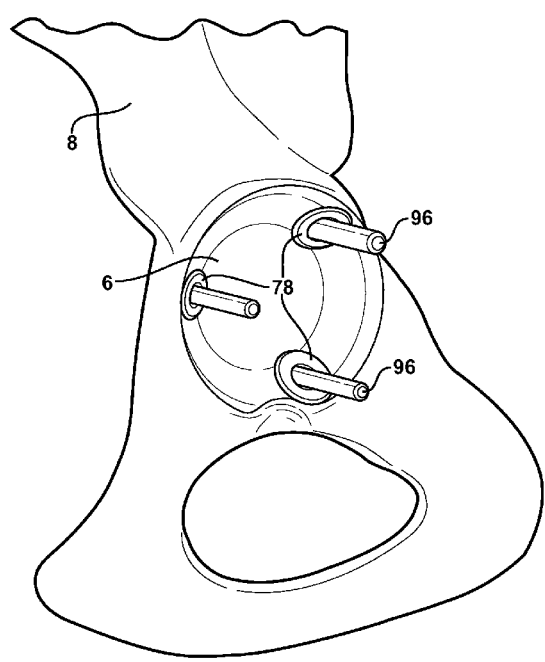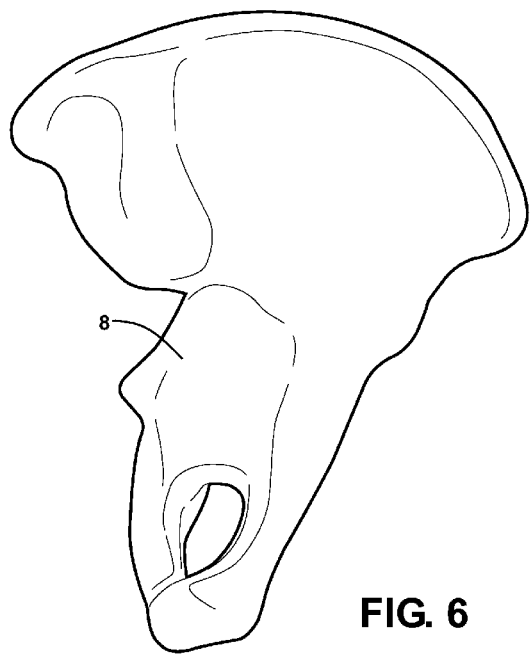
FIG. 5
FIG. 6

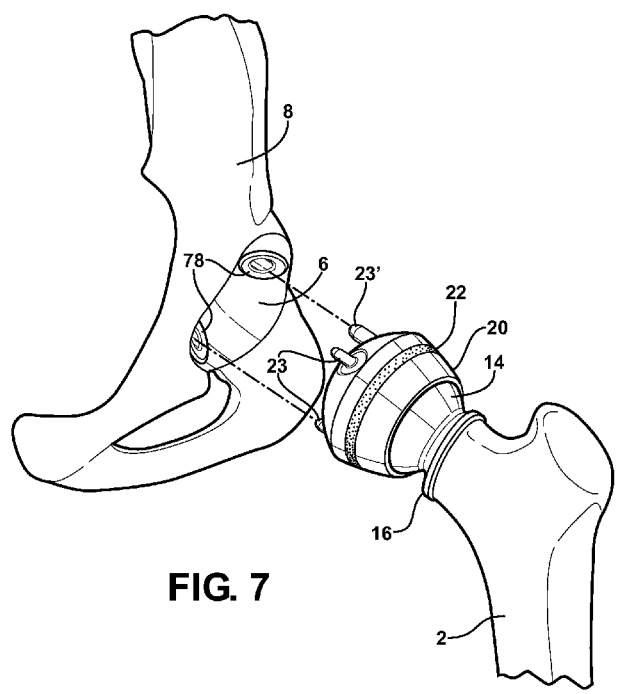
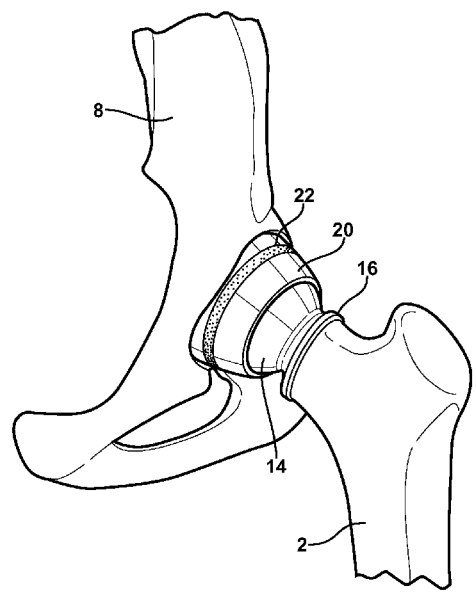
FIG. 7
FIG. 8

COMBINATION MALE/FEMALE HIP JOINT AND INSTALLATION KIT

FIELD OF THE INVENTION

The present invention relates generally to replacement assemblies for use in the acetabulofemoral (i.e. hip) joint. More particularly, the present invention teaches a self-contained and replaceable articulating hip utilized in a hip arthroplasty procedure, as well as an installation kit for assisting the preparation of the femur and ilium bones defining the hip joint, as well as the installation of the implant body into the upper conditioned femur end and the outer socket support to a reconditioned acetabulum defined in the ilium bone.

BACKGROUND OF THE INVENTION

The prior art is documented with various types of hip replacement assemblies. These typically include either the removal and/or refashioning of the insertable head associated with the thigh or upper femur bone along with the receiving acetabulum socket defined in the pelvic area located ilium bone. Such replacement hip assemblies con also incorporate artificial or synthetic implant components, however their relative large size contributes to an attendant degree of installation effort and patient discomfort associated with its surgical implantation.

SUMMARY OF THE INVENTION

The present invention discloses a hip implant assembly including body exhibiting a substantially spherical shaped ball and an elongated stem. An annular defining rim separates the ball from the stem and abuts, in a maximum inserting condition, an exterior surface of a reconditioned femur upon inserting the stem within an interior passageway associated with the femur.

A three dimensional and interior volume defining support secures around the ball in a universally articulating permitting fashion. The support is affixed to a reconditioned acetabulum socket associated with an ilium bone by interconnecting posts and anchors established between the fixed support and the reconditioned surface of the acetabulum.

Additional features include the body and support being constructed of any type of plastic, metal or admixture thereof, and an inner remote end of the stem being cored or otherwise recess machined in order to promote the in-growth of marrow within the and around the stem. A plurality of entrapped lubricant defined passageways are located between the ball and an overlaying surface of the support. A venting port is incorporated into an interior socket configuration established between the support and ball in communication with the interior passageways to permit the removal, venting and/or replacement of the lubricant fluid.

The outer socket mounting support may also include a generally cup-shape defining a receiver for seating the ball and including a softer and inner/arcuate absorbing layer extending in embedded fashion between an inner facing surface and an outer facing surface seating against the acetabulum socket. The annular extending flange of the body may also constructed of a softer grade material than either the stem and ball to assist in shaping and form fitting about an exposed reconditioned surface of the upper femur.

A plurality of outwardly projecting posts integrally formed with an exposed surface of the support are dimensioned to seat within apertures defined in the reconditioned acetabulum socket. A plurality of anchors are installed within the apertures in an undercut engaging manner defined within the acetabulum socket, the posts extending from the support and seating within the apertures. The anchors can further be recess fitted within holes formed in the ilium bone and in an undercut engaging fashion.

Other features include an overlap configuration established between an end extending rim of the support and inner seating ball which is located posterior to the maximum width/diameter dimension of the ball. In this fashion, the ball is retained in seating fashion within the outer affixed and recess configuring support, while concurrently permitting a maximum possible degree of universal movement of said ball relative to said support without causing the rim edge to come into contact with the flange defining the boundary between the insertable stem and ball.

An outwardly displaceable anchor is further defined within the stem is actuated by a rotatable input to screw surface mounted in said annular flange. A series of interior and interconnected linkages are incorporated into the stem of the body and transfer a rotatable input applied to the annular flange located and surface exposed screw to outwardly displace the anchor into biasing contact with the interior of the femur, causing the flange to be drawn tight against the reconditioned surface of the femur. A subset variant also includes the one piece ball and supporting stem reconfigured as a pair of threadably engageable components, such that the ball includes an externally threaded shaft end which is threadably engaged with an inner threaded surface associated with a mating interior passageway of the stem and in proximity to the annular flange.

Yet additional features include a plurality of outwardly projecting posts with enlarged dimensioned ends mounted to the reconditioned acetabulum and resistively fitting within internal anchors configured within an increased dimensioned base of the support. In another variant, a first plurality of radial positioned posts with button projections is mounted to the reconditioned acetabulum, a matching plurality of recessed slots being configured upon the mounting surface of the support and including enlarged and perimeter defined inserting portions at an initial locating and inserting position. The outer socket support and ball are subsequently twist locked an incremental angular direction within the slots so that the button projections are caused to resistively seat within reduced dimensioned portions associated with each of the recess defined slots.

In another variant, a plurality of displaceable anchors are located in spaced fashion about an outermost periphery of the support and which are seated in linearly projecting fashion through perimeter spaced internal apertures defined in spaced apart fashion about the periphery of the support. Each the anchors include enlarged resistance engaging end which are linearly displaced into and in resistive engaging contact with previously defined undercut recesses formed about a corresponding perimeter of the acetabulum socket.

A yet further variant includes a plurality of circumferentially spaced and outwardly displaceable tabs disposed about a width periphery of the support and seated within associated recesses formed in the support. The tabs are outwardly displacing and downwardly rotating in successive motions and in order to overlay surrounding and spaced surface locations of the ilium bone in a precise and fit-adjustment fashion. A plurality of anchors are incorporated into the tabs and engage the bone. A like plurality of tab locking pins are mounted to the support at peripheral locations aligning with the tabs and which are downwardly displaced to fix the tabs at their extended and rotated positions concurrent with them being anchored in place to the ilium bone.

An associated installation kit for assisting the preparation of the femur and ilium bones defining the hip joint, as well as the installation of the implant body into the upper conditioned femur end and the outer socket support to a reconditioned acetabulum defined in the ilium bone, includes a saw for removing a damaged bulbous shaped head associated with the femur and in order to reveal a generally annular shaped receiving face which communicates an interior extending passageway. A hand held grinder exhibiting a hemispherical shaped and rotatably driven grinder bit reshapes the acetabulum socket to match a mounting surface associated with the outer socket support.

A drill fixture template is mounted to the ilium bone and overlays the reconditioned acetabulum, the template including a plurality of apertures arranged in a desired pattern array. A drill is insertable in succession into through each of the apertures defined in the template and in order to create an initial hole within the acetabulum. A subsequent undercut pattern is formed within a recessed side wall location of the hole, such as made possible by undercut engaging lateral blade portions associated with the drill.

A plurality of posts secure to either of said holes in the acetabulum or to the mounting surface of the outer socket support and in order to engaging the outer socket to the reconditioned acetabulum. In one embodiment, the posts project linearly from the outer socket support mounting surface and are resistively engaged within deformable anchors pre-fitted into the undercut machined holes in the ilium bone in communicating fashion with the acetabulum.

Additional features of the installation kit include the hemispherical shaped grinder bit of the hand held grinder further exhibiting a plurality of individual incising blade portions arranged in a longitudinal arrayed pattern. A three dimensional open interior created within a tool head of the grinder between a base and the hemispherical bit providing for collection of bone shavings and debris, these vacuum removed for storage within a waste chamber located in a rear handle.

The drill template further exhibits edge extending engagement tabs temporarily mounted to specified surface locations of the ilium bone. The drill further exhibits a fluted exterior configured and elongated bit, a secondary shaft extending linearly within a recess within the elongated bit and which is actuated via gear drive components built into a base of the bit to linearly elevate the shaft into engagement with a pair of progressively outward laterally and displaceable undercut machining bits seated within lateral passageways defined in the bit. Also provided are a plurality of recess anchors constructed of a durable and flexible/expandable plastic and which are sized so as to be installed within a previously formed drill hole with undercut profile.

BRIEF DESCRIPTION OF THE DRAWINGS

Reference will now be made to the attached drawings, when read in combination with the following detailed description, wherein like reference numerals refer to like parts throughout throughout the several views, and in which:

FIG. 3 is an illustration of a portable and hand held rotary ball shaped grinder, such as can be provided as an attachment secured to a rotary drill motor and which includes built in vacuum retrieval of debris, the grinder being utilized in situ within the patient for refashioning/resizing the associated acetabulum socket defined in the lateral base of the ilium and between the pubis and ischium branches;

FIG. 3A is a further partial illustration of a modified grinder provided as a drill attached bit;

FIG. 4 is an illustration of a successive installation step following the rotary grinder of FIG. 3 in the arthroplasty procedure and by which the a drill fixture template is mounted to the previously refashioned cavity, the fixture including an array of apertures for receiving a further drill in order to create a pattern within the recessed interior of the previously reformed socket;

FIG. 4A is a further partial illustration of a modified drill exhibiting a bit attachment end;

FIGS. 4B and 4C illustrate a modified drill bit for creating an undercut profile within each of the holes formed through the template into the refashioned socket;

FIGS. 4D, 4E and 4F illustrate examples of protruding/expanding barbs incorporated into recess anchors installed within previously undercut defined drill holes;

FIG. 5 is a succeeding illustration in which the drill fixture template is removed and the a series of installation anchors are fitted into the undercut recess formed holes;

FIG. 6 is a substantially rotated generally back side of the ilium in FIG. 5 and illustrating the reshaping of the acetabulum socket and the installation of the anchors occurring within the interior of the bone and without breaching the rear side;

FIG. 7 is an overall view of the assembly secured to the upper thigh bone as shown in FIG. 2 in partially exploded array relative to the previously reformed acetabulum of FIG. 5;

FIG. 8 is a further successive assembled view in which the femur, ball and socket are aligned and subsequently assembled by inserting into the recessed defined anchors a plurality of posts arrayed in projecting fashion from the surface of the integrated articulating assembly;

DETAILED DESCRIPTION OF THE PREFERRED EMBODIMENTS

The present invention teaches a self-contained and replaceable articulating hip utilized in a hip arthroplasty procedure. The ball, socket/receiver and associated stem components can be constructed of any type of plastic, metal or admixture according to any desired ration or percentage. As will be also described, the implant components can be provided with varying hardness/softness to maximize both comfort and wear, and it is further understood that the present assembly provides for a maximum degree of implant efficiency, universality in use and degree of comfort to the patient.

Figure 1:
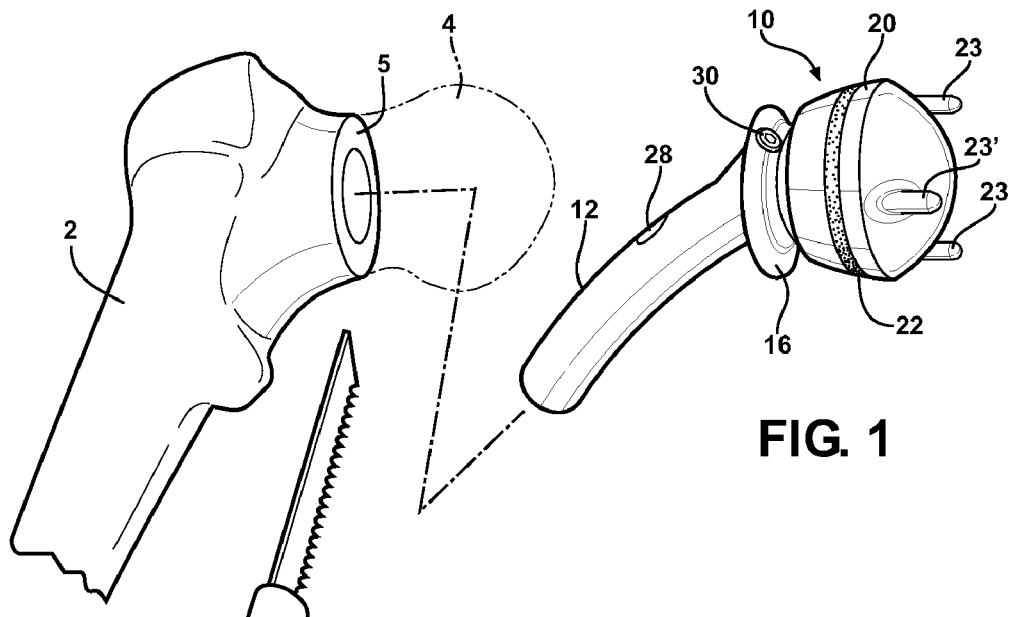
FIG. 1 is a partially exploded view of the upper femur illustrating in phantom outline the removed ball and further showing the implant assembly including insert stem and articulating head which integrates both the ball and socket components into a single and universally articulating assembly.
Figure 2:
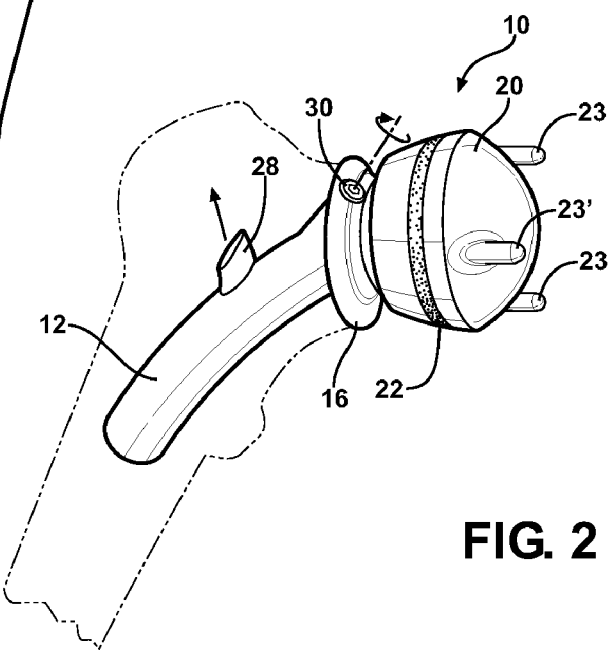
FIG. 2 is a successive installed view of the assembly in FIG. 1, and further showing the feature of the outwardly displaceable anchor associated with an embedded stem location and which is actuated by a rotatable input applied to a screw incorporated into a rim surface location of the implant assembly.

FIGS. 1 and 2 illustrate both partially exploded and assembled views, genitally at 10, of the combined installation stem and exposed end supported and universally articulating head which can be installed into a reconditioned and channel defined end of an upper femur (thigh bone) 2 of a patient, and typically such as following reconditioned removal of the previously existing (and typically compromised or damaged) bulbous shaped head of the upper femur 2, this further illustrated at 4 in phantom and which is normally accomplished with the use of an appropriate medical saw or like power reciprocated or chain drive, as well as manually reciprocated instrument, see at 3 in FIG. 1. As previously described, and upon reconditioning the upper femoral end (see as exhibiting a smoothed and generally annular shaped receiving face 5) and the subsequent installation of the replacement assembly including the insert stem and articulating head, the ball and socket components are integrated into a single and universally articulating assembly which mimics that of the natural ball and socket.

Figure 11:
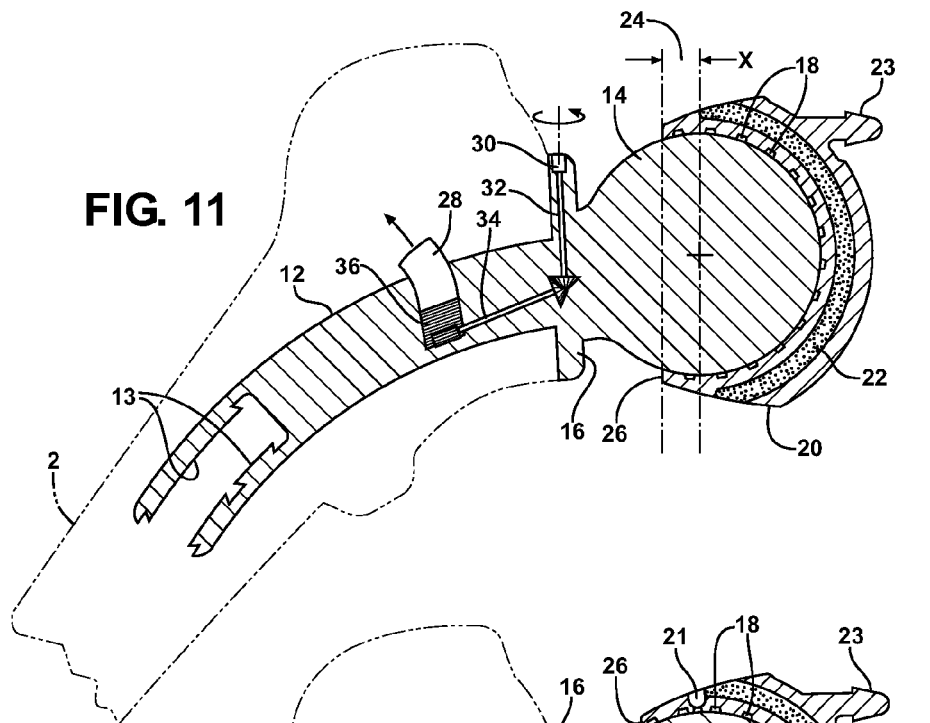
FIG. 11 is a generally lengthwise cutaway illustration of the assembly according to any of the previously identified variants and illustrating the configuration established between the inner universally articulating ball and outer affixed support, this further showing both the features of entrapped lubricant defined passageways established at the interface between the inner ball and outer support, the configuration of the remote extending end of the stem for facilitating marrow bonding, and the ability to size the overlapping dimension of the outer affixed support at any location posterior to the maximum width/diameter dimension of the inner ball and in order to retain the ball within the outer affixed and recess configuring support while permitting a maximum degree of universal movement of the ball.

As supplemented by the lengthwise cutaway view of FIG. 11, the implant assembly exhibits a generally elongated and arcuate stem 12 which is supported within the interior passageway associated with the upper femur bone 2. The stem 12 can be adhesively cemented within the femur bone interior (such as through the application of a polymethylmethacrylate) and it is further envisioned that an inner remote end of the stem 12 can be cored or otherwise recess machined, see as shown 13, in order to promote the in-growth of marrow within the and around the inserted end of the stein 12 and to improve long term anchoring support of the stern within the bone.

A generally spherical or ball shaped head 14 is integrally formed with the stem 12 and, as shown, is separated by an interposed and annular surface exposed rim 16 which defines an installation limit of the stein 12 within the conditioned and passageway defined bone interior. The generally lengthwise cutaway illustration of the assembly further illustrates a plurality of entrapped lubricant defined passageways, at 18 and which are established at the interface between the inner ball 14 and a three dimensional shaped and interior volume defining outer support 20, which is in turn anchored within the acetabulum defined socket interior (see at 6 in FIG. 3) of the ilium (at 8), such as between the lower extending pubis and ischium tributaries. As further shown in the variant of FIG. 11A, a venting port 21 can be incorporated into the interior socket configuration established between the support 20 and ball 14 and in communication with the interior passageways 18 to permit the removal, venting and/or replacement of the lubricant fluid.

As further shown in FIG. 11, the outer ball receiving and universal articulating support 20 can each again be constructed of any type of plastic or metal (or mixture), the support 20 further exhibiting a generally cup-shape defining a receiver for seating the ball 14 and including a softer and inner/arcuate absorbing layer 22 extending in embedded fashion between the inner facing surface within which is established the ball/lubricant passage 18 defined boundary, and the exposed outer surface of the support 20 which is in turn anchored within the acetabulum socket 6 in a manner to be subsequently described.

Figure 12:
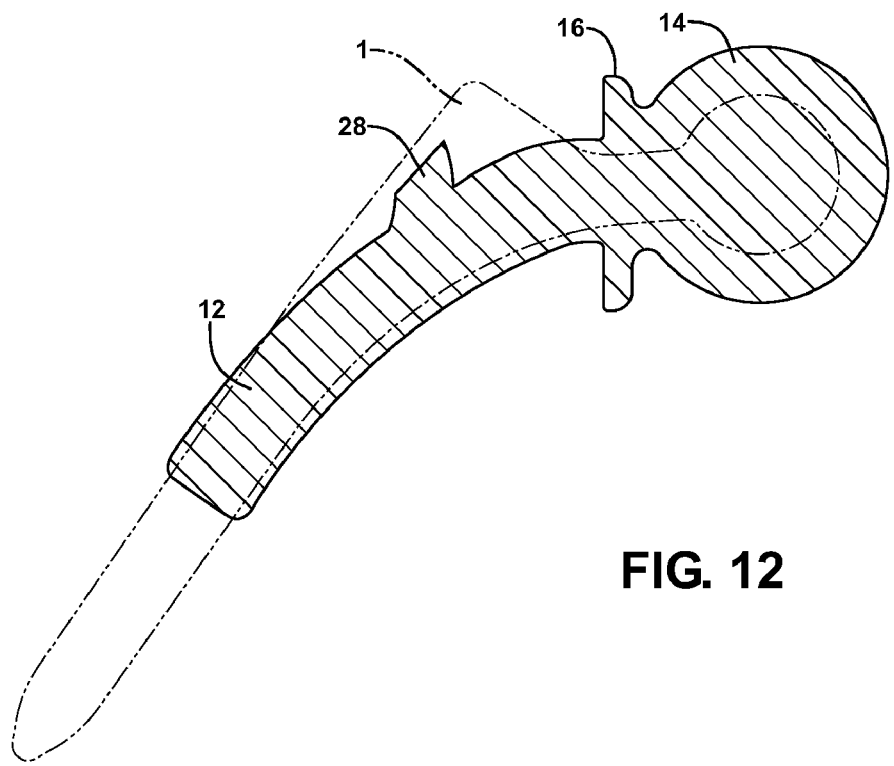
FIG. 12 is an overlap illustration comparing an insert stem and ball according to the present invention in overlapped relationship relative to a conventional ball and stein implant, further shown in phantom.

It is further understood that the annular extending flange 16 can be constructed of a softer grade plastic or other material as compared to either or both the stem 12 or ball 14, this assisting in more easily shaping and form fitting of the flange 16 about the exposed reconditioned surface of the upper femur 2. As shown in FIG. 12, an overlap illustration compares the insert stem and ball according to the present invention in overlapped relationship relative to a conventional ball and stem implant, further shown in phantom at 1, and which demonstrates the advantages of the current design both as to reduced overall length and increased socket dimension.

Also shown at 23 are a plurality of forward projecting posts (with a larger selected post shown at 23') and which are integrally formed with the exposed and seating outer surface of the support 20. As will be described in subsequent detail, the posts 23 are provided to facilitate anchoring of the outer fixed support 20 within the reconditioned acetabulum socket 6.

Further illustrated at 24 is a spaced dimension corresponding to an overlap configuration or dimension established between an end extending rim 26 of the affixed outer support 20 and the and any location of the inner seating ball 14 which is located posterior to the maximum width/diameter dimension of the ball, this in order to retain the ball in seating fashion within the outer affixed and recess configuring support 20, while at the same time permitting a maximum possible degree of universal movement of the ball 14 relative to the anchored support 20 without causing the rim edge 26 to come into contact with the annular exposed surface rim 16 defining the boundary between the insertable stem 12 and the exposed ball 14.

As further illustrated in both FIGS. 1, 2 and 11, the feature of an outwardly displaceable anchor 28 is shown associated with an embedded stem 12 location, and which is actuated by a rotatable input such as to a rotatable screw 30 incorporated into the annular rim surface location 16 of the implant assembly. The linear cutaway of FIG. 11 further illustrates a series of interior and interconnected linkages, see at 32 and 34, which transfer the rotatable input applied to the screw 30 (this such as by a tool or other suitable keyed implement) and which cause an end-rotatable component, see further shown at 36 and which is operated by the turning of the selected linkage 34, to in turn outwardly displace the anchor 28 (such as which can be influenced by a suitable ratcheting or inter-teethed arrangement) outwardly and in biasing contact with the interior of the upper thigh bone. As is further shown, the forward/upward angle associated with the upper surface configuration of the anchor 28 is such that, upon it being actuated outwardly and against the inner surface of the femur bone in communication with the inner passageway, the stem 12 and annular flange 16 are caused to be biased inwardly within the femur 2 and further so that the annular surface flange 16 is pulled tight against the reconditioned femur surface as shown in FIG. 2.

Figure 11A:
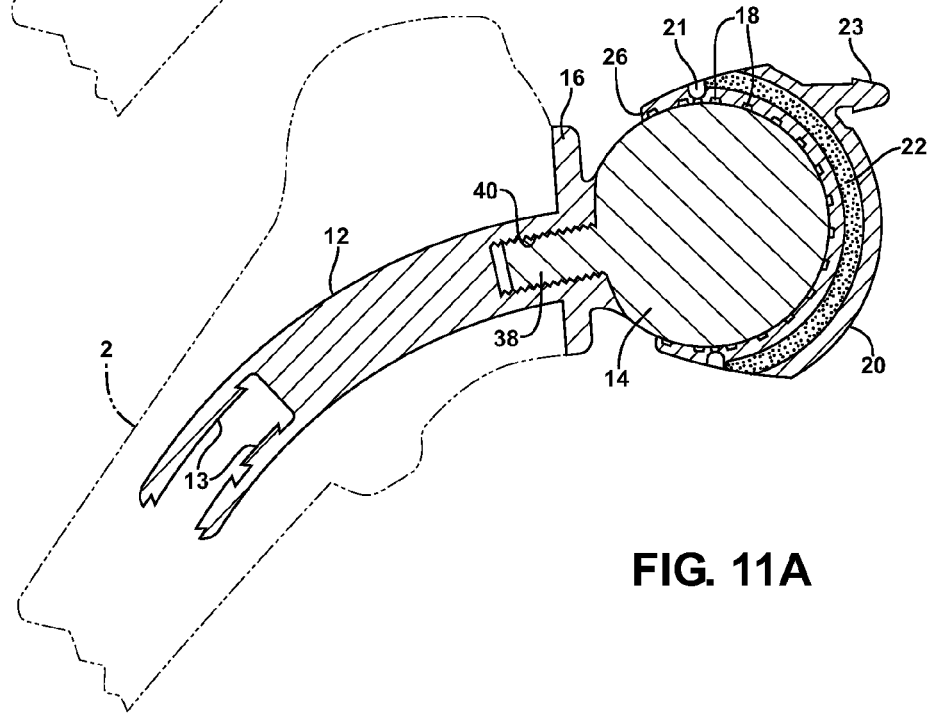
FIG. 11A is an illustration of a slight variant of the assembly in FIG. 11 and in which the one piece ball and supporting stem of FIG. 11 can be reconfigured into a pair of threadably or otherwise inter-engageable components.

The actuation linkage demonstrated is intended to show only one of a number of potentially varying mechanisms for outwardly displacing an anchor for providing an additional degree of fixed support to the stem, this in addition to either or both the use of adhesives and/or the notching or inner end coring of the stem in order to promote the natural growth of bone marrow. It is further understood that various combinations of some or all of these implant retaining features can be utilized in order to secure the implant assembly in place upon the reconditioned bone end and concurrent with FIG. 11A is an illustration of a slight variant of the assembly in FIG. 11 and in which the one piece ball 14 and supporting stein 12 of FIG. 11 is reconfigured into a pair of threadably or otherwise inter-engageable components. This includes the ball 14 having an externally threaded shaft end 38 which is threadably engaged with an inner threaded surface 40 associated with a mating interior passageway associated with the stem 12 and in proximity to the abutment stop defining annular flange 16. In this fashion, a damaged ball 14 can be removed and replaced without the requirement of retrieval/removal of the interior anchored stem 12.

Referring now to FIG. 3, an illustration of a portable and hand held rotary ball shaped grinder, such as shown at 42 and which can be provided as a self contained and powered unit or, as alternatively depicted in FIG. 3A, as an attachment 43 secured to a separate rotary drill motor (not shown). The rotary grinder 42 exhibits a hand held gripping body and, at a forward end, terminates in a generally hemispherical seating portion 44 within which is rotatably supported (such as via a drive shaft extending longitudinally along an interior of the tool 42 from a powered input located in the handle) a further hemispherical shaped and rotating grinder bit 46 and which is rotated by the inner drive shaft.

As is further illustrated, the hemispherical shaped grinder bit 46 exhibits a plurality of individual incising blade portions 48 which are arranged in a longitudinal arrayed pattern. Upon being placed over the acetabulum socket 6 of the ilium bone 8, this again being defined in the lateral base of the ilium and between the pubis and ischium branches, the grinder 42 is activated in order to progressively shave bone from the acetabulum 6, causing its socket profile to eventual match the exterior profile of the hemispherical bit 46. A three dimensional open interior is created within the tool head between the base 46 and attached hemispherical bit 48 and provides for collection of bone shavings and debris, these subsequently being vacuum removed from the grinding head for storage within such as a waste chamber located in a rear handle or other portion of the grinder 42 for subsequent emptying.

FIG. 4 is an illustration of a successive installation step following the rotary grinder 42 of FIG. 3 according to the arthroplasty procedure, and by which the a drill fixture or template 50 exhibiting a generally disk shape with edge extending engagement tabs 52 is provided and is temporarily mounted via the tabs 52 engaging specified surface locations of the ilium bone 8 in order to cover the previously refashioned acetabulum cavity. As shown, the fixture includes an array of apertures 54 (such as three shown) for receiving a further and specially modified drill 56 in order to create a precise drill pattern within the recessed interior of the previously reformed socket 6. As with the rotary grinder 42, the modified drill 56 can be self-powered or, as shown at 57 in FIG. 4A, can be provided as a bit attachable to a separate hand-held and powered unit. As with the rotary grinder 42, the further modified chill 56 vacuum evacuates and stores, such as within an internal waste chamber not shown but evident from the body shown at 56 in FIG. 4, bone debris created from the internal holes drilled through the aperture pattern in the template 50.

Figure 10:
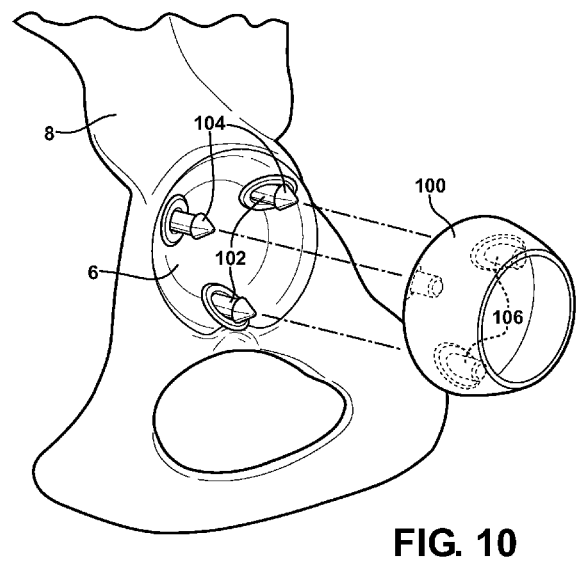
FIG. 10 is a partially exploded illustration of a further variant and in which a plurality of hip anchors with mounting posts are formed within the reshaped acetabulum and which exhibit enlarged projecting ends which resistively fit within recesses formed in an installed fixed outer articulating support associated with the implant assembly.

An objective of the hole pattern formed through the use of the template 50 and the drill such as shown at 56 is the eventual engagement of anchors or posts (as will be further described in reference to the related variants of FIGS. 5, 7, 10, et seq.) either within or extending from the inwardly concave reconditioned surface of the acetabulum socket. To facilitate this engagement, it is desirable for form an undercut or other suitable enlarged/dovetailed pattern within the initially formed drill hole (again such as three defined in the apertured pattern established by the template).

To this end, FIGS. 4B and 4C illustrate a modification associated with the drill 56 and its associated forming bit, this in order to create a desired undercut profile within each of the holes formed through the template into the refashioned socket. FIGS. 4B and 4C illustrate a first example of a specific design of drill bit 58, this exhibiting a suitable fluted exterior pattern and which is integrally rotated along with input shaft 60.

Following completion of the initial drill hole within the ilium bone interior (and as dictated by the placement of apertures within the disk template 50), a secondary and interior shaft, at 62, is seated within a linear passageway defined in said bit 58 and is actuated to linearly/outwardly displace such as via gear drive components 64 built into a base housing 66 and which coact with a suitable mating teethed or other desirable pattern formed in a base of the inner displaceable shaft 62. A pair of laterally displaceable undercut defining bits 68 and 70 each exhibit an underside taper, see at 72 and 74 in FIG. 4B. The bits 68 and 70 are seated within lateral passageways defined proximate a tip of the bit 58 and, upon the inner shaft 62 being upward displaced, its pointed tip 76 (again FIG. 4B) causes the secondary lateral bits 68 and 70 to be laterally displaced outwardly in an incremental and progressive fashion in order to create the desired undercut profile. Following this, the inner shaft 62 is retracted and the lateral bits 72 and 74 automatically retract upon exerting a removal force to the overall bit body 58.

Given the precise and in situ nature of the bone machining process, it is further desirable to provide both the initial drill hole and secondary undercut hole using the same tool and in a quickly succeeding nature, with the undercut being located at any internal position of the initial drill hole in order to correspond to the configuration of any subsequently installed retaining post or anchor. That said, it is also envisioned and understood that the feature of the undercut formation can be provided by a separate drill bit with spring out portions such as described above or the like, and which may be inserted within a template defined aperture following completion of the primary drill hole by a more conventionally configured bit.

Referring now to FIGS. 4D, 4E and 4F, illustrated are examples respectively shown at 78, 80 and 82, of a variety of different types of recess anchors, each of which being constructed of a durable and flexible/expandable plastic in a generally balloon or condom-like shape within an open bottom end and which are sized so as to be installed within a previously formed drill hole with undercut profile according to the forming procedures of FIGS. 4 and 4B/4C. Each of the recess anchors further incorporate a protruding or expanding barb, see respective profiles 84 for FIG. 4D (matching laterally displaceable bits 68 and 70), at 86 for FIG. 4E (incorporating pairs of dovetail undercut patterns for engaging linearly spaced undercut profiles formed in the previous drill hole via a suitable drill tool or the manipulation of a tool such as shown in FIGS. 4B/4C which relocates the undercut bits to a secondary location) and finally at 88 for FIG. 4F (generally balloon shaped profile for seating within an enlarged and more bulbous shaped undercut profile achieved with a suitable tool).

As is fluffier shown in FIGS. 4D-4F, the open bottom ends of the individual configured anchors 78, 80 and 82 are each configured with an internal pattern or the like profile, this further shown at 90, 92 and 94, respectively and which facilitates collapsing and expansion of the various barb projections built into the anchors. Upon pre-inserting within the individually formed template drill holes, the anchors are pulled tight (this occurring manually or through the application of a farther inwardly collapsing pullers as shown at 96 in FIG. 5) causing the anchors to completely fill and the drill holes and undercut profile in an anchored and withdrawal prevented fashion. Once completely tightened, the pullers 96 can be broken off and/or linearly retracted to reveal the inwardly mounted anchors (such as again profiled at 78 in the example of FIG. 4D) secured within the previously undercut formed drill holes. FIG. 6 is a substantially rotated generally back side of the ilium 8 in FIG. 5 and which is intended to illustrate the reshaping of the acetabulum socket and the subsequent formation of the undercut drill holes and installation of the anchors within the interior of the bone, this occurring without breaching the rear side of the ilium 8.

Figure 9:
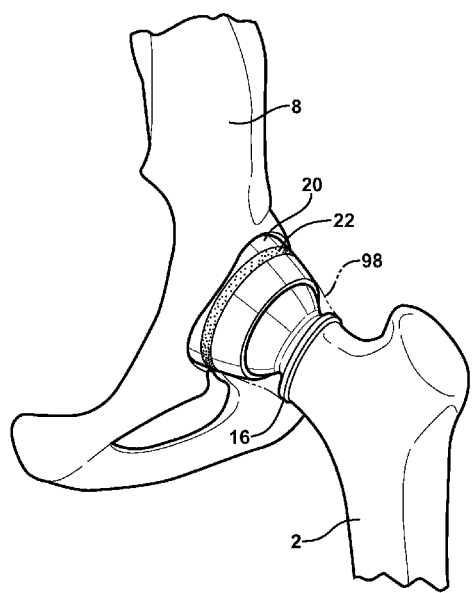
FIG. 9 is an illustration largely similar to that shown in FIG. 8 and by which the combined ball and socket is shown in comparison to a dimension in phantom illustrative of an original ball socket and to which the implant assembly closely matches in dimension.

Proceeding to FIG. 7, an overall view of the assembly 10 as previously described is shown secured to the upper thigh bone (also as previously depicted in FIG. 2) and subsequently positioned in partially exploded array relative to the previously reformed acetabulum of FIG. 5. The mating face of the outer anchoring support 20 (from which extend the inserting posts 23 and 23') can exhibit any of a smooth, roughened or undercut configuration in order to facilitate either dry, cemented or bone promoting growth upon the posts 23, 23' being installed within the various anchors 78 and installing to the ilium 8 (as shown in FIG. 8) and so that the femur 2 is secured in a universally articulating fashion closely mimicking that of a natural hip socket. Referring now to FIG. 9, is an illustration largely replicating that shown in FIG. 8 and by which the combined ball and socket is shown in comparison to a corresponding original profile (shown in phantom at 98) associated with an original ball and socket connection.

The larger/longer illustrated post illustrated at 23' (as compared to additional smaller sized posts 23) extending from the forward seating face of the outer socket support 20 is shown configured with a unique shape (e.g. such as being longer or differently shaped) and an associated undercut hole and anchor can be likewise configured in mating fashion. By keying the post 23' to a selected anchor 78, incorrect attachment of the socket is avoided. Additional variants also contemplate the socket exhibiting any number or configuration of posts and/or anchors.

Also not shown but understood to be provided is any arrangement of ligament or connective structure between the outer socket support 20 and the reformed acetabulum socket. Such can include the posts 23 and 23' being reconfigured to resistively fit or otherwise engage within the undercut formed profile associated with each drill aperture. It is also understood and envisioned that any type of naturally forming and/or artificial ligament structure can be provided (not shown), such as replicating the traditional five types of ligaments of which four are extracapsular (iliofemoral, ischiofemoral and pubofemoral (2)) and one intracapsular (liagmentum teres). Also not shown but understood to be present both in the presently disclosed structure and succeeding description of the associated arthroplasty procedure are the features of reconstructed vein, nerve and muscle connections, these borrowing from both existing and novel techniques and procedures for creating an effective and durable artificial hip implant.

Referring now to FIG. 10, a partially exploded illustration is shown of a modified and three dimensional shaped support 100 for securing and retaining in universal articulating fashion the inner socket ball (not shown), this according to a further variant in combination with a plurality of revised configured hip posts 102 exhibiting forward increased dimensioned projecting ends 104 formed or otherwise installed within the reshaped acetabulum 8. The posts 102 with enlarged dimensioned ends 104 resistively fit within internal anchors 106 configured within a suitably dimensioned (and thickened) base of the fixed outer support 100 and so that the position of the anchors and inserting posts do not interfere with the articulating motion of the installed socket ball. Upon being aligned and press fit, the revised support 100 operates in an identical fashion to that previously described.

Figure 10A:
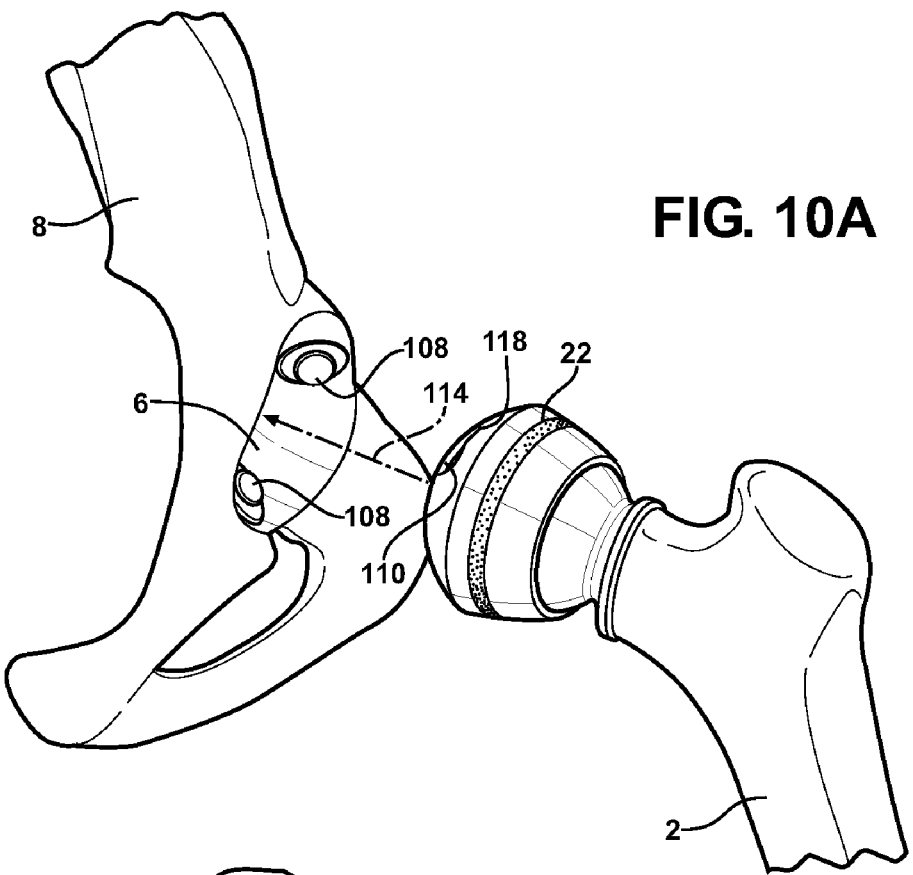
FIG. 10A is a partially exploded illustration of a further twist and lock variant of the hip joint assembly and in which a first plurality of radial positioned posts with button projections are formed within the refashioned acetabulum and seat within a matching plurality of slots defined in the exposed fashion of the outer articulating support which are subsequently rotated causing said posts to resistively seat within reduced dimensioned portions of said slots.
Figure 10B:
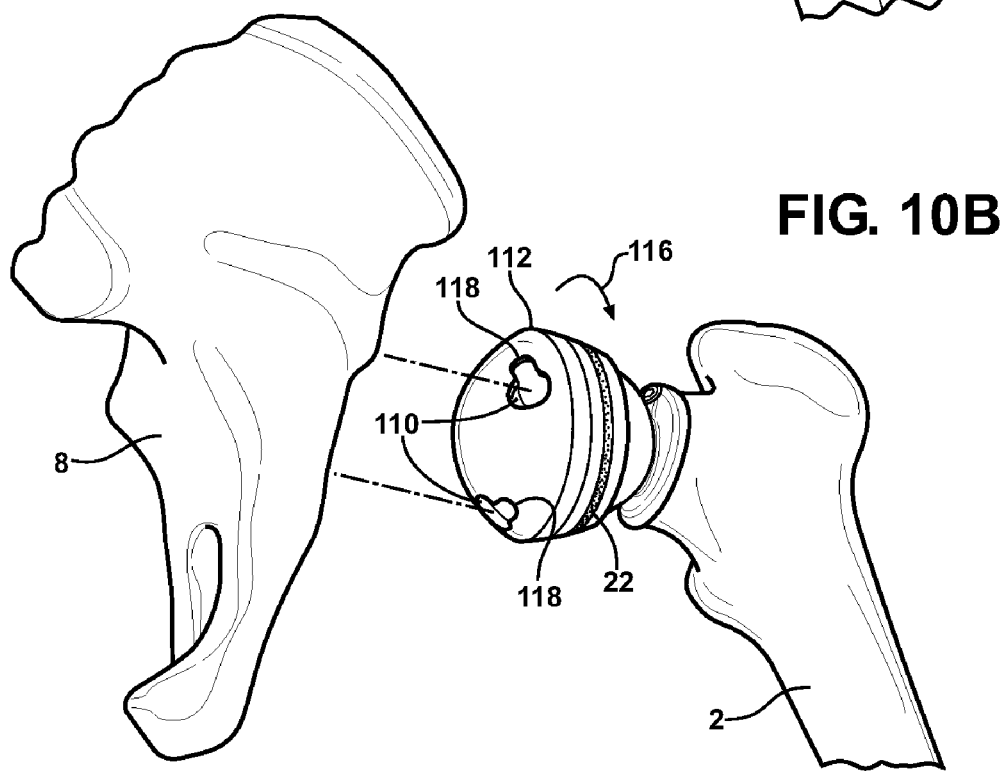
FIG. 10B is a rotated perspective of the partially exploded view of FIG. 10A and better showing the configuration of the rotary extending slots with enlarged insert and reduced dimension twist and lock portions.

FIG. 10A is a partially exploded illustration of a further twist and lock variant of the hip joint assembly and in which a first plurality of radial positioned posts 108 with button projections are formed within the refashioned acetabulum 6 and which seat within a matching plurality of slots including an enlarged inserting perimeter 110 defining a first initial locating and inserting position (FIG. 10B) which is accessible from an exposed and seating surface of a further redesigned three dimensional articulating support 112. Upon initial linear installation (see arrow 114 in FIG. 10A), the socket and ball is caused to be twist locked an incremental angular and clockwise rotation (see further directional arrow 116 in FIG. 10B) and which the button configured projections are subsequently caused to resistively seat within reduced dimensioned portions 118 associated with each of the recess defined slots 110.

Figure 13:
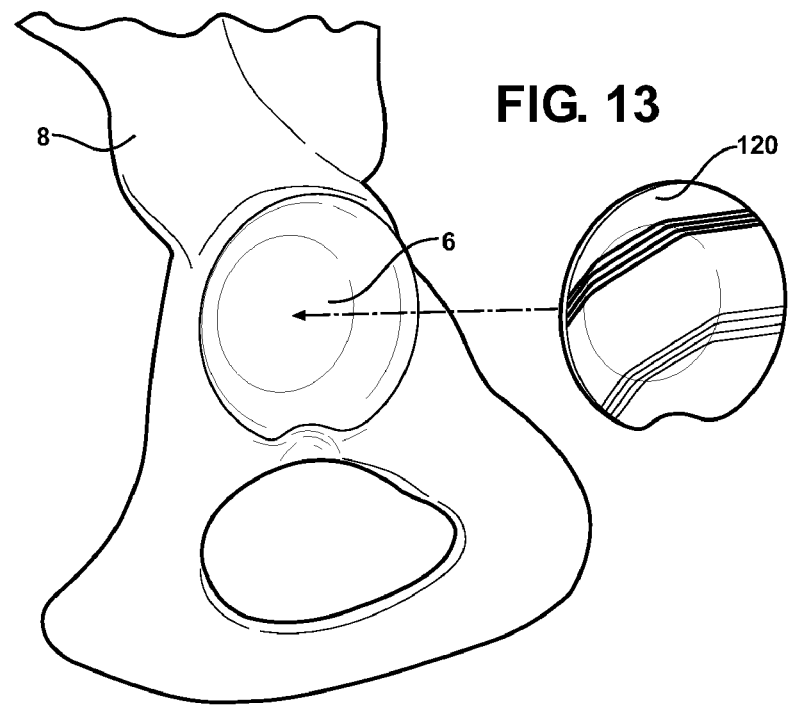
FIG. 13 is a perspective of the acetabulum socket defined in the hip ilium and illustrating in partially exploded fashion a hip socket liner constructed of either or an admixture of both a metal and a plastic and which is cemented or otherwise secured to a previously reconditioned acetabulum surface prior to installation of the universal ball.

Referring now to FIG. 13, a perspective illustration is again shown of the acetabulum socket 6 defined in the hip ilium and illustrating, in partially exploded fashion, a hip socket liner 120 constructed of either or an admixture of both a metal and a plastic and which is cemented or otherwise secured to a previously reconditioned acetabulum surface prior to installation of the universal ball and outer socket support (not shown). It is contemplated that any part of the hip socket (i.e. ilium bone 8), can be constructing of or lined with a layering of any type of plastic, metal or admixture thereof.

Figure 14:
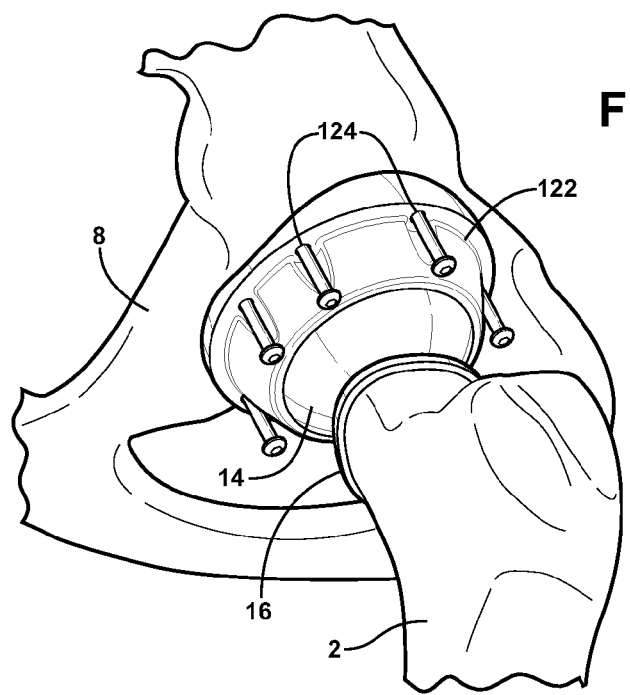
FIG. 14 is an illustration of an installation assembly according to a yet further embodiment and in which a plurality of displaceable anchors are located in spaced fashion about an outermost periphery of the outer affixed housing containing the socket and ball for installation within the acetabulum socket.

FIG. 14 is an illustration of an installation assembly according to a yet further embodiment and in which a redesigned outer and socket defining anchoring support 122 is provided. A plurality of displaceable anchors 124 are located in spaced fashion about an outermost periphery of the outer affixed support housing containing the socket and ball for installation within the acetabulum socket in a manner consistent with that previously described. As further shown, the anchors 124 generally correspond to spike-shaped components and which are seated in linearly projecting fashion through perimeter spaced internal apertures (not shown) defined in spaced apart fashion about the periphery of the three dimensional and socket housing outer support 122.

Figure 15:
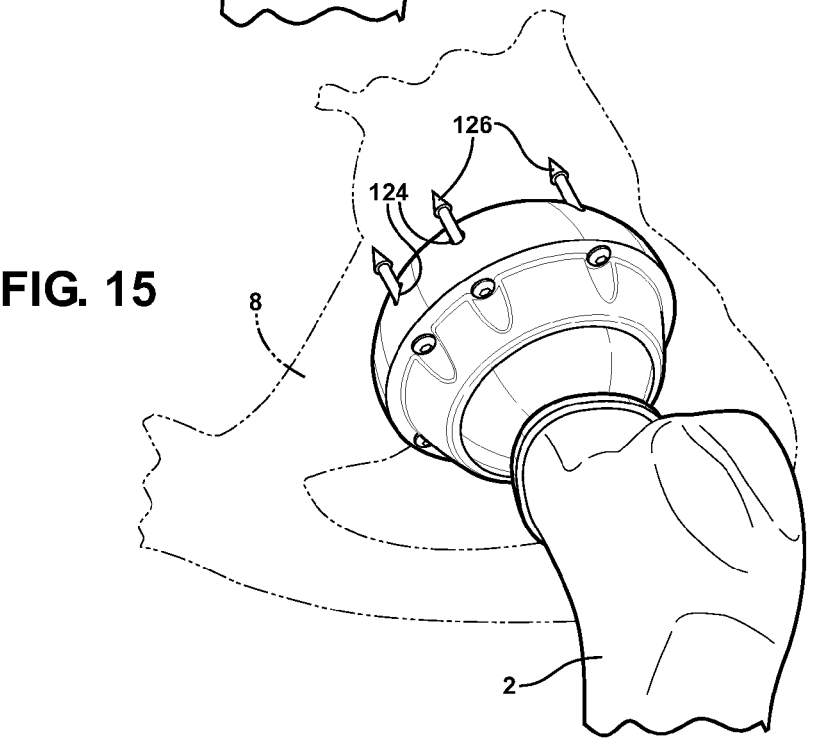
FIG. 15 is a succeeding illustration to FIG. 14 in which the ilium bone is shown in phantom and by which the anchors are linearly displaced into previously defined undercut recesses formed about a corresponding perimeter of the acetabulum socked associated with the ilium bone.

FIG. 15 is a succeeding illustration to FIG. 14 in which the ilium bone 8 is shown in phantom and by which the anchors 124 each include enlarged resistance engaging ends 126 which are linearly displaced into previously defined undercut recesses (not shown but understood as being capable of formed according to any of the structures and assembly protocols previously described) formed about a corresponding perimeter of the acetabulum (socket) associated with the bone. It is further understood that the anchors 124 can be provided as any of pre-drilled, self-drilling, barbed, twisting, push pin or other expanding type structure. Furthermore, it is envisioned that the support 122 can be redesigned to feature any amount or configuration of anchors encircling the socket.

Figure 16:
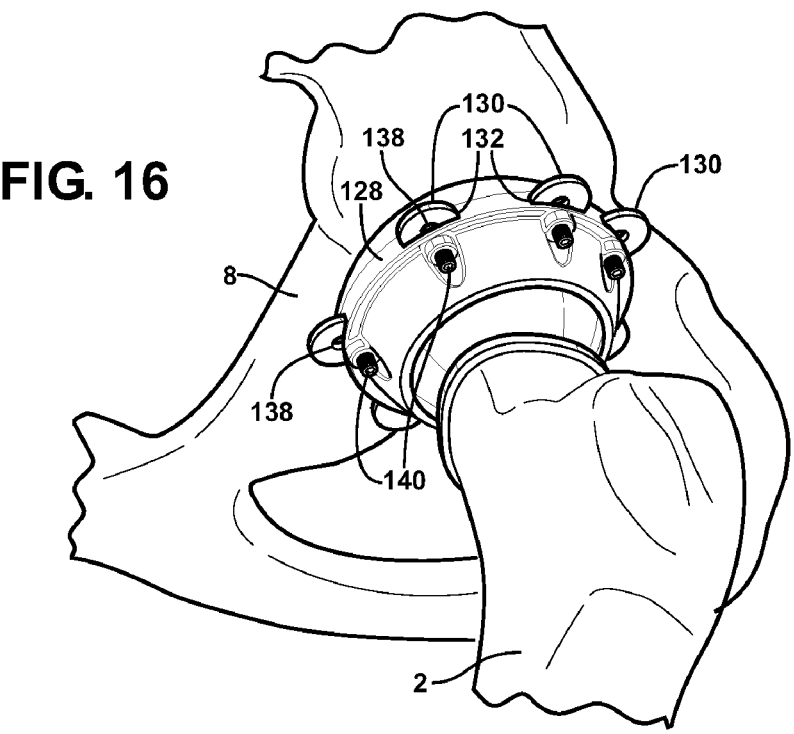
FIG. 16 is an illustration of a yet further installation assembly in which a plurality of laterally outwardly displaceable tabs are associated with the outer affixed housing.
Figure 17:
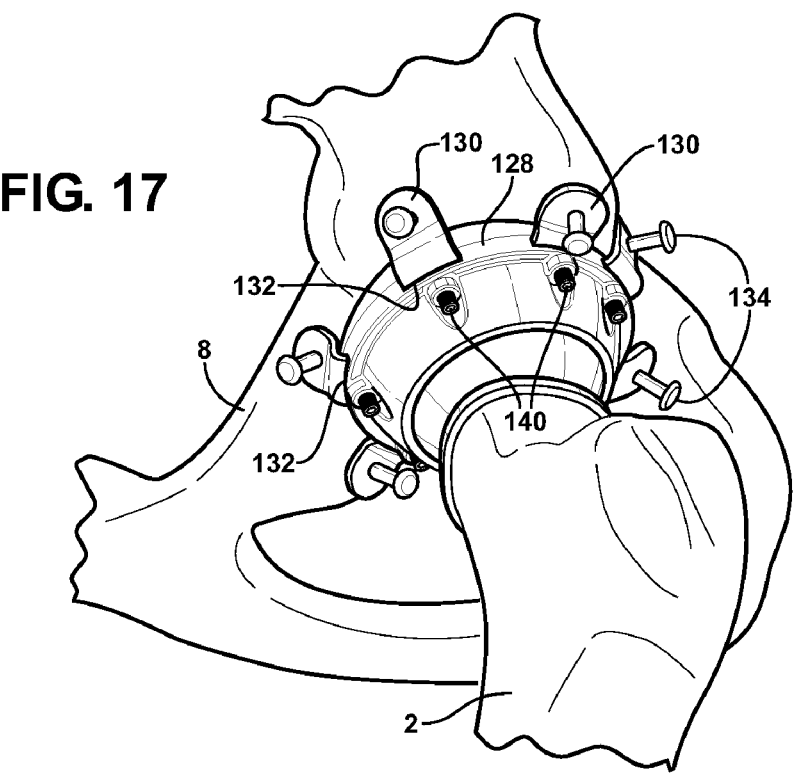
FIG. 17 is a succeeding view to FIG. 16 in which, upon aligning the outer fixed articulating support within the acetabulum, the tabs are outwardly displaced and downwardly rotated in successive motions in order to overlay surrounding and spaced surface locations of the ilium bone.
Figure 18:
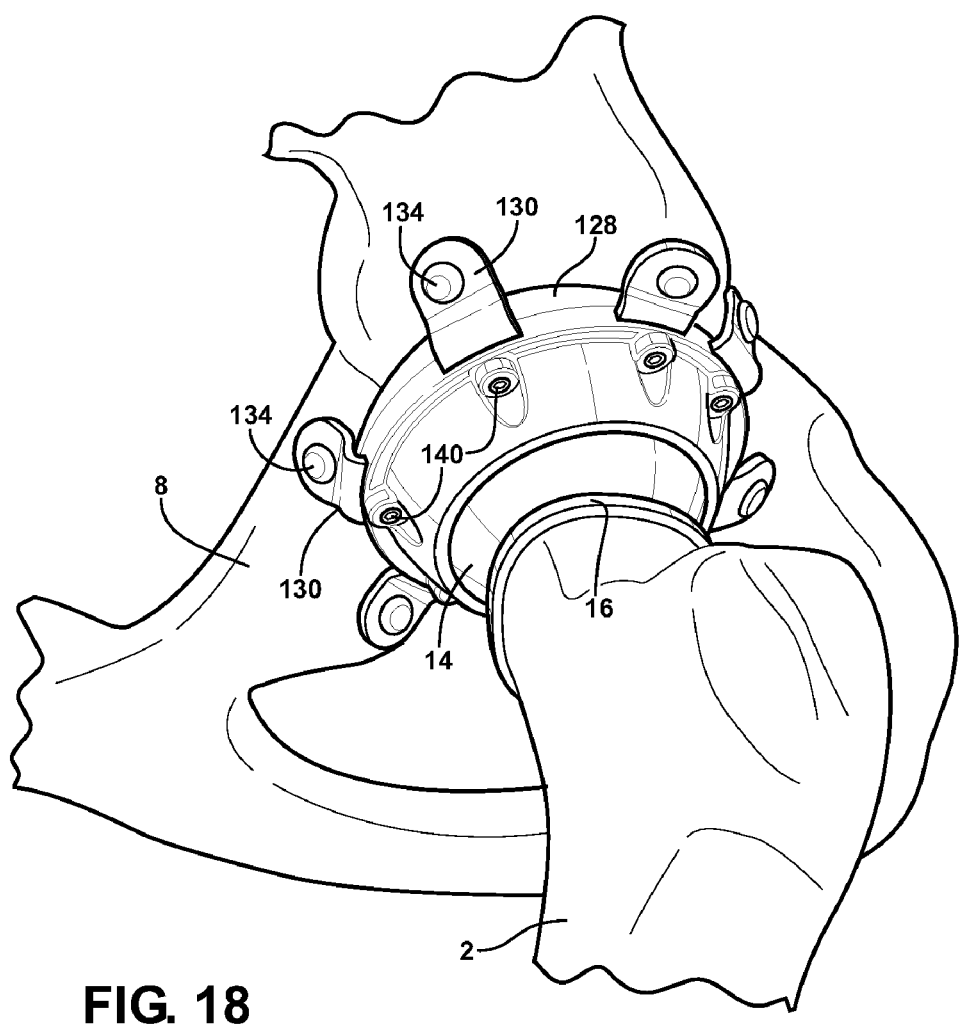
FIG. 18 is a final assembled view in which a plurality of anchors built into the tabs are caused to seat within drill formed and receiving recesses spot located within the ilium bone, concurrent with associated tab locking pins being downwardly displaced to lock the tabs into their extended positions.

Finally, and referring to FIGS. 16-18, a series of illustrations are shown of a yet further configuration of outer fixed and three dimensional socket housing or support 128 for anchoring to the previously reformed/refashioned acetabulum socket. The support 128 exhibits a widened width periphery approximate to which are located a plurality of circumferentially spaced apart and outwardly displaceable tabs 130, these being seated within associated recesses defined by inner facing perimeter surfaces 132.

FIG. 17 is a succeeding view to FIG. 16 in which, upon aligning the outer fixed support 128 within the acetabulum, the tabs 130 are outwardly displaced and (further owing to their angled profiles) are downwardly rotated in successive motions and in order to overlay surrounding and spaced surface locations of the ilium bone 8 in a precise and fit-adjustment fashion. FIG. 18 is a final assembled view in which a plurality of anchors 134 either built into or separately attachable to the tabs are caused to seat within end proximate apertures 138 of each tab (see FIG. 16).

Although not shown, it is understood that any of the preceded described forming processes can be employed in order to drill form receiving, including undercut, recesses such as spot located within the ilium bone in a simultaneous/concurrent fashion. A final installation step includes the provision of associated tab locking pins 140 designed into the architecture of the housing support 128 and at peripheral locations aligning with the tabs 130 in their fully extended position of FIG. 17. Although not shown, it is understood that inner holes are provided in a base portion of each tab 130 which align with the inserting direction of the locking pins 140 and which are downwardly displaced to fix the tabs 130 into their extended positions concurrent with them being anchored in place to the ilium bone 8.

Having provided a detailed description of the working components of the hip installation assembly according to the several variants, a description will now be made of the associated procedure for placement, in situ with the patient, of the self-contained articulating total hip arthroplasty device which is self lubricating, and totally constrained, thereby preventing the occurrence of undesirable dislocations.

As is known, standard exposure for total hip arthroplasty via anterior, anterolateral, poster approaches include soft tissue dissections and corresponding arthrotomies. Acetabular (ilium socket) preparation through acetabular reamers (e.g. rotary drill of FIG. 3) shape the acetabulum (socket) into a desired hemispherical shape. Debris to be removed through the self-accumulating grinder is collected in a waste chamber associated with the acetabular grinder body.

The placement of the reconditioned acetabular shell (socket) is such that it is located at a customary articulating position of anteversion and horizontal inclination per the host (patient) anatomy. Fixation pegs for the acetabular anchoring devices are created through drilling into the acetabular bone stock (FIG. 4). The anchoring pegs/pins/screws are then placed into the host acetabular bone stock. At this point, the drill template (again FIG. 4) is removed and placement of the host socket acetabulum is mated to the fixation devices of the articulating acetabular femoral, self contained construct. Fixation of the acetabulum (socket) may be augmented with bone in-growth surfaces (again shown in the linear cutaway of the supporting stem in FIG. 11) such as exhibiting macro/micro textures to provide osteo-integration to the acetabular surface.

The femoral (upper thigh bone) preparation created in a standard femoral neck osteotomy procedure includes adequately defining the entrance into the intramedullary canal of the femur (FIG. 1). Reconditioning preparation of the femur can include broaching such as is created by reaming, drilling, broaching of the proximal femur to accept the configuration of the femoral implant. The self contained device incorporating the acetabular articular surfaces and the femoral head articulating surface are manufactured in a self contained single unit which provides a range of motion anatomically similar to a hip joint, thus preventing the occurrence of dislocation of the femoral head away from the acetabulum, and is self-lubricating for improved longevity (see FIGS. 11 and 11A). The new femoral head diameter and corresponding socket exhibit a similar profile in size and configuration to that of the patient's original anatomy.

The device is then inserted into the femoral canal (FIG. 2) and either press-fit or cement mantle with an adhesive compound such as a polymethylmethacrylate to a fully seated position. The feature of the stem extending articulating keel slot (also previously termed as displaceable anchor as again shown in FIG. 2) is again provided to prevent loosening or migration of the femoral implant.

The total articulating device, now entered into the femoral canal to a full seated position is then inserted with pegs/pins/screw fixation and the like into the acetabular component where it is engaged. As described in reference again to FIG. 11, the overlap arrangement established between the fixed and outer receiving support and the inner seating ball defines a resultant range of universal motion.

Also previously described, the ball and socket articulating device can be constructed of a metal, plastic or any admixture or inter-percentage defined composite to provide any of a range of desired material properties. The femoral inserted and supporting stem can also be manufactured to exhibit either of a cemented or non-cemented macro or micro texture to allow bone fixation or growth (again exhibited by the interior configuration associated with the stein in FIG. 11) into the component.

The acetabular component may also be constructed of a bone in-growth promoting macro or micro texture and which may also exhibit shock absorbing layers of polymers and/or plastics to prevent shock absorbing affect to the acetabulum and to prevent the incidence of stress transmission to the interfaces of the acetabulor or femoral implant. The phalange of the neck of the femoral prosthesis may also exhibit a softer material than either metals or ceramics to thereby allow shock absorbing affect with the interface of the femoral component.

The femoral stem itself may be made of metal or plastic and, as previously described, the integrally formed or separably attachable acetabular component may be combinations of metal, plastic and polymers. It is also envisioned that the articulation of the head relative to the receiving socket (again FIG. 11) will be manufactured to maximize stability, range of motion and protection of the wear surfaces.

Having described my invention, other and additional preferred embodiments will become apparent to those skilled in the art to which it pertnins, and without deviating from the scope of the appended claims.

I claim:

1. A hip implant assembly, comprising:
a body including a substantially spherical shaped ball from which extends an elongated stem, an annular defining flange separating said ball from said stem and adapted to abut an exterior surface of a reconditioned femur upon inserting said stem within an interior passageway associated with the femur;
an outwardly displaceable anchor within said stem which is actuated by a rotatable input to a screw surface mounted in said annular flange, a series of interior and interconnected linkages are incorporated into said body and transfer a rotatable input applied to said screw to outwardly displace said anchor into biasing contact with the interior of the femur, causing said flange to be drawn tight against the reconditioned surface of the femur; and
a three dimensional and interior volume defining support securing about said ball in a universally articulating permitting fashion, said support further comprising a mounting surface mating with and affixed to a configuration associated with a reconditioned acetabulum socket of an ilium bone.

2. A hip implant assembly, comprising:
a body including a substantially spherical shaped ball from which extends an elongated stem, an annular defining flange separating said ball from said stem and adapted to abut an exterior surface of a reconditioned femur upon inserting said stem within an interior passageway associated with the femur;
a three dimensional and interior volume defining support securing about said ball in a universally articulating permitting fashion, said support further comprising a mounting surface mating with and affixed to a configuration associated with a reconditioned acetabulum socket of an ilium bone; and
a plurality of outwardly projecting posts with enlarged dimensioned ends adapted to mount to the reconditioned acetabulum and resistively fitting within internal anchors configured within an increased dimensioned base of said support.

3. The invention as described in claim 2, further comprising said stem adapted to being adhesively cemented within the femur bone interior.

4. The invention as described in claim 2, further comprising an inner remote end of said stem being cored or otherwise recess machined in order to promote the in-growth of marrow within the and around said stem.

5. The invention as described in claim 2, further comprising a plurality of entrapped lubricant defined passageways established between said ball and an overlaying surface of said support.

6. The invention as described in claim 5, further comprising a venting port incorporated into an interior socket configuration established between said support and ball and in communication with said interior passageways to permit the removal, venting and/or replacement of the lubricant fluid.

7. The invention as described in claim 2, further comprising each of said support and body being constructed of any type of plastic, metal or admixture.

8. The invention as described in claim 2, said support further comprising a generally cup-shape defining a receiver for seating said ball and including a softer and inner/arcuate absorbing layer extending in embedded fashion between an inner facing surface and an outer facing surface adapted to seat against the acetabulum socket.

9. The invention as described in claim 2, further comprising said annular extending flange constructed of a softer grade material than said stem and ball to assist in shaping and form fitting about an exposed reconditioned surface of the upper femur.

10. The invention as described in claim 2, further comprising an overlap configuration established between an end extending rim of said support and inner seating ball which is located posterior to the maximum width/diameter dimension of said ball in order to retain the ball in seating fashion within the outer affixed and recess configuring support while concurrently permitting a maximum possible degree of universal movement of said ball relative to said support without causing said rim edge to come into contact with said flange defining the boundary between said insertable stem and ball.

11. The invention as described in claim 2, further comprising said ball and elongated stem configured as a pair of threadably engageable components, said ball including an externally threaded shaft end which is threadably engaged with an inner threaded surface associated with a mating interior passageway of said stem and in proximity to said annular flange.

12. A hip implant assembly, comprising:
a body including a substantially spherical shaped ball from which extends an elongated stem, an annular defining flange separating said ball from said stem and adapted to abut an exterior surface of a reconditioned femur upon inserting said stem within an interior passageway associated with the femur;
a three dimensional and interior volume defining support securing about said ball in a universally articulating permitting fashion, said support further comprising a mounting surface mating with and affixed to a configuration associated with a reconditioned acetabulum socket of an ilium bone; and a first plurality of radial positioned posts with button projections mounted to the reconditioned acetabulum, a matching plurality of recessed slots being configured upon the mounting surface of said support and including enlarged and perimeter defined inserting portions at an initial locating and inserting position, said socket and ball subsequently being twist locked an incremental angular direction within said slots so that said button projections are caused to resistively seat within reduced dimensioned portions associated with each of the recess defined slots.

13. A hip implant assembly, comprising:

a body including a substantially spherical shaped ball from which extends an elongated stem, an annular defining flange separating said ball from said stem and adapted to abut an exterior surface of a reconditioned femur upon inserting said stem within an interior passageway associated with the femur;

a three dimensional and interior volume defining support securing about said ball in a universally articulating permitting fashion, said support further comprising a mounting surface mating with and affixed to a configuration associated with a reconditioned acetabulum socket of an ilium bone; and a plurality of displaceable anchors located in spaced fashion about an outermost periphery of said support and which are seated in linearly projecting fashion through perimeter spaced internal apertures defined in spaced apart fashion about the periphery of said support, each of said anchors include enlarged resistance engaging end which is linearly displaced into and in resistive engaging contact with previously defined undercut recesses adapted to form about a corresponding perimeter of the acetabulum socket.

14. A hip implant assembly, comprising:

a body including a substantially spherical shaped ball from which extends an elongated stem, an annular defining flange separating said ball from said stem and adapted to abut an exterior surface of a reconditioned femur upon inserting said stem within an interior passageway associated with the femur;

a three dimensional and interior volume defining support securing about said ball in a universally articulating permitting fashion, said support further comprising a mounting surface mating with and affixed to a configuration associated with a reconditioned acetabulum socket of an ilium bone; and a plurality of circumferentially spaced and outwardly displaceable tabs disposed about a width periphery of said support and seated within associated recesses formed in said support, said tabs outwardly displacing and downwardly rotating in successive motions and in order to overlay surrounding and spaced surface locations of the ilium bone in a precise and fit-adjustment fashion, a plurality of anchors incorporated into said tabs and engaging the bone, a like plurality of tab locking pins mounted to said support at peripheral locations aligning with said tabs and which are downwardly displaced to fix said tabs at their extended and rotated positions concurrent with them being anchored in place to the ilium bone.

\* \* \* \* \*

UNITED STATES PATENT AND TRADEMARK OFFICE
CERTIFICATE OF CORRECTION

PATENT NO. : 8,328,875 B2
APPLICATION NO. : 12/649456
DATED : December 11, 2012
INVENTOR(S) : Miguel A. Linares Page 1 of 1

It is certified that error appears in the above-identified patent and that said Letters Patent is hereby corrected as shown below:

In the Specifications:

At column 1, line number 24, Delete "con", Insert -- can --

At column 6, line number 2, Delete "genitally at 10", Insert -- generally at 10 --

At column 6, line number 29, Delete "stein 12", Insert -- stem 12 --

At column 8, line number 43, Delete "chill", Insert -- drill --

At column 9, line number 50, Delete "as is fluffier", Insert -- as is further --

At column 9, line numbers 57-58, Delete "farther inwardly", Insert -- further inwardly --

At column 11, line numbers 43-44, Delete "the bone", Insert -- the ilium bone --

At column 13, line number 15, Delete "stein", Insert -- stem --

Signed and Sealed this
Thirtieth Day of April, 2013

Teresa Stanek Rea
*Acting Director of the United States Patent and Trademark Office*